(12) United States Patent
Modi

(10) Patent No.: US 7,255,102 B2
(45) Date of Patent: Aug. 14, 2007

(54) METERED DOSE SPRAY DEVICE FOR USE WITH MACROMOLECULAR PHARMACEUTICAL AGENTS SUCH AS INSULIN

(75) Inventor: Pankaj Modi, Ancaster (CA)

(73) Assignee: Generex Pharmaceuticals Inc., Toronto, Ontario (CA)

( * ) Notice: Subject to any disclaimer, the term of this patent is extended or adjusted under 35 U.S.C. 154(b) by 224 days.

(21) Appl. No.: 10/061,856

(22) Filed: Feb. 1, 2002

(65) Prior Publication Data

US 2006/0067891 A1    Mar. 30, 2006

(51) Int. Cl.
*A61M 11/00* (2006.01)
*A61M 16/20* (2006.01)
*A61K 9/12* (2006.01)

(52) U.S. Cl. .................... 128/200.14; 128/200.23; 128/200.21; 128/203.11; 424/45; 514/3

(58) Field of Classification Search ........... 128/200.14, 128/200.16, 200.23, 200.21, 203.11; 424/45, 424/43, 46, 54, 435; 514/3
See application file for complete search history.

(56) References Cited

U.S. PATENT DOCUMENTS

| | | | |
|---|---|---|---|
| 5,536,444 A | 7/1996 | Hettche et al. | |
| 5,676,129 A | 10/1997 | Rocci, Jr. et al. | |
| 5,681,545 A | 10/1997 | Purewal et al. | |
| 5,826,571 A | 10/1998 | Casper et al. | |
| 6,138,669 A | 10/2000 | Rocci, Jr. et al. | |
| 6,228,346 B1 * | 5/2001 | Zhang et al. | 424/45 |
| 6,427,682 B1 * | 8/2002 | Klimowicz et al. | 128/200.14 |
| 6,485,706 B1 * | 11/2002 | McCoy et al. | 424/45 |
| 6,964,759 B2 * | 11/2005 | Lewis et al. | 424/45 |

FOREIGN PATENT DOCUMENTS

| | | | |
|---|---|---|---|
| EP | 0 949 584 A2 | | 10/1999 |
| GB | 2 367 011 A | * | 3/2002 |
| WO | WO97/33640 | | 9/1997 |
| WO | WO 98/24420 | | 6/1998 |

OTHER PUBLICATIONS

J.J. Sclarra and A.J. Cutie, "Aerosols", Chapter 93, pp. 1662-1677.

* cited by examiner

*Primary Examiner*—Johann Richter
*Assistant Examiner*—Mina Haghighatian
(74) *Attorney, Agent, or Firm*—Hamilton, Brook, Smith & Reynolds, P.C.

(57) ABSTRACT

A metered dose spray device administers medicine contained therein to the buccal cavity within a user's mouth upon actuation of the device. A metered dose spray device comprising an insulin solution is also provided.

15 Claims, 3 Drawing Sheets

METERED DOSE SPRAY DEVICE FOR USE WITH MACROMOLECULAR PHARMACEUTICAL AGENTS SUCH AS INSULIN

FIELD OF THE INVENTION

The present invention is directed to a metered dose spray device for administering medication to the buccal cavity of a user's mouth. The invention also relates to a metered dose spray device comprising a solution of a macromolecular pharmaceutical agent such as insulin, and a method of dispensing a solution of a macromolecular pharmaceutical agent using a metered dose spray device.

BACKGROUND OF THE INVENTION

Medications such as insulin must presently be administered by subcutaneous injection. Such injections are painful, resulting in refusal among diabetics to administer the required doses at the appropriate times. Additionally, the absorption of the insulin is affected by the site of the injection, the temperature of the tissue, the vascularity of the tissue, and the activity of the underlying muscle. Failure to properly deliver the appropriate insulin doses to properly regulate blood sugar results in development of various complications of diabetes, such as blindness.

Metered dose spray devices are presently used to administer many different medications to the mouth and lungs, for example, asthma medication and nitroglycerin for treatment of heart disease. A typical metered dose spray device includes a can for containing a solution or suspension of medication, a metering valve, and an actuator. The can will contain the medication to be dispensed, possibly a solvent for the medication, and a propellant. The propellant is a substance having a low boiling point and high vapor pressure, so that as liquid is dispensed from the container the propellant evaporates, maintaining a constant pressure within the can. Actuation of the metering valve causes the metering chamber within the valve to close with respect to the can, and open with respect to the mouthpiece. Propellants within the metering chamber will evaporate due to the sudden decrease in pressure when the valve is actuated, propelling the medication into the user's mouth.

Presently available metered dose spray devices are not suitable for dispensing medication that is to be absorbed through the buccal cavity. A suitable dispenser must dispense appropriately sized particles at an appropriate velocity to penetrate the tissue covering the blood vessels within the buccal cavity, and must dispense a suitable volume to ensure that the portion actually reaching the buccal cavity represents the desired dose. Additionally, the device must not clog, which could prevent administering a dose when one is needed during a diabetic emergency. Furthermore, if insulin is the desired medication, the spray device must contain an insulin formulation adapted for buccal cavity delivery. Present metered dose inhalers typically dispense too little volume to ensure reliable buccal cavity delivery of a desired dose, and produce a fine aerosol mist of particles less than 5 microns in size, increasing the likelihood of inhalation of the medication into the lungs. The particles are not directed towards any specific portion of the mouth, but are placed generally inside the mouth where they may be inhaled or absorbed. Therefore, if the medication dispensed is insulin, use of a presently available metered dose spray device would result in possible side effects associated with lung delivery. Therefore, a metered dose spray device dispensing a sufficiently high quantity of medication, at a sufficiently high pressure, to ensure that a sufficient quantity will be propelled into the buccal cavity for proper absorption of the desired dose, is necessary.

Accordingly, an insulin formulation adapted for buccal cavity delivery is desired. Additionally, a metered dose spray device adapted for administering large-molecule medications such as insulin to the buccal region is desired.

SUMMARY OF THE INVENTION

The present invention is directed to a metered dose spray device dimensioned and configured to administer a medication contained therein to the buccal cavity within the user's mouth. Although not limited to such use, such a metered dose spray device is particularly useful for administering insulin. A metered dose spray device comprising a suitable insulin formulation is also provided.

Generally, the metered dose spray device consists of three major components; an aerosol can, containing medication in liquefied propellant gas; a metering valve, which when depressed dispenses a known quantity of the medication; and a buccal spray actuator which when combined with the stem of the metering valve comprises an expansion chamber, also called a sump, and a nozzle, often called a spray orifice. The actuator itself is comprised of an actuator boot, stem block, sump, spray orifice and mouthpiece. The actuator boot keeps the aerosol can fixed in place. The stem block is dimensioned and configured to receive the stem of the metering valve, which is fixed to the aerosol can, and whose purpose is to carry the medication from the metering valve to the actuator sump, specially designed to act as an expansion chamber and to redirect the aerosol through the spray orifice, whose geometry prevents the possibility of clogging.

In the rest position, the metering chamber of the valve is connected directly to the aerosol can containing the medication. Upon depression of the can and valve stem, this connection is closed and the metered discharge process begins. The metered dose is ejected from the metering chamber under the pressure of the flashing liquid propellant. The medication then passes through the valve stem orifice into the actuator sump where it undergoes further boiling as it attempts to fill the chamber and displace the air. Finally, a high-quality spray, particularly suited to buccal delivery, emerges from the spray orifice and mouthpiece of the actuator.

The present metered dose spray device is particularly useful for permitting diabetics to administer insulin to themselves in a manner more convenient than injections. A metered dose spray device of the present invention delivers medications into the oral cavity in the form of appropriately-sized particles travelling at an appropriate velocity for absorption through the buccal mucosa and thus the medication is not inhaled into the lungs, thereby avoiding possible side effects associated with lung delivery.

Although not limited to administering insulin, a metered dose spray device of the present invention may also contain an insulin formulation adapted for buccal cavity delivery. Such a formulation includes insulin molecules, micelle-forming substances, and absorption enhancers, so that the insulin molecule is covered by a protective coating. Upon actuation of the device, the coating of the insulin permits it to penetrate the tissue covering the blood vessels in the buccal cavity if dispensed at a sufficiently high velocity, and assists in its absorption into the bloodstream. The insulin formulation of the present invention, administered by a device of the present invention, will appear in circulation within 10 minutes.

It is therefore an aspect of the present invention to provide a metered dose spray device dimensioned and configured to administer medication to the buccal cavity of the user's mouth.

It is another aspect of the present invention to provide a metered dose spray device having a metering valve with a metering chamber sufficiently large so that a high volume of medication will be forced through an actuator sump and spray orifice having a small volume upon actuation of the metering valve.

It is a further aspect of the present invention to provide a metered dose spray device having an actuator sump and spray orifice with a suitable geometry and diameter so that medication is administered at high pressure and velocity.

It is another aspect of the present invention to provide a metered dose spray device suitable for administering insulin.

It is a further aspect of the present invention to provide an improved dose counter.

These and other aspects of the present invention will become more apparent through the following description and drawings.

BRIEF DESCRIPTION OF THE DRAWINGS

Like reference numbers denote like elements throughout the drawings.

DETAILED DESCRIPTION

The present invention is directed to a metered dose spray device for administering insulin to the buccal cavity within the user's mouth. A metered dose spray device having an insulin solution is also provided.

Referring to the figures, the metered dose spray device 10 includes an actuator 12, an aerosol can 14, and a metering valve 16.

Figure 2:
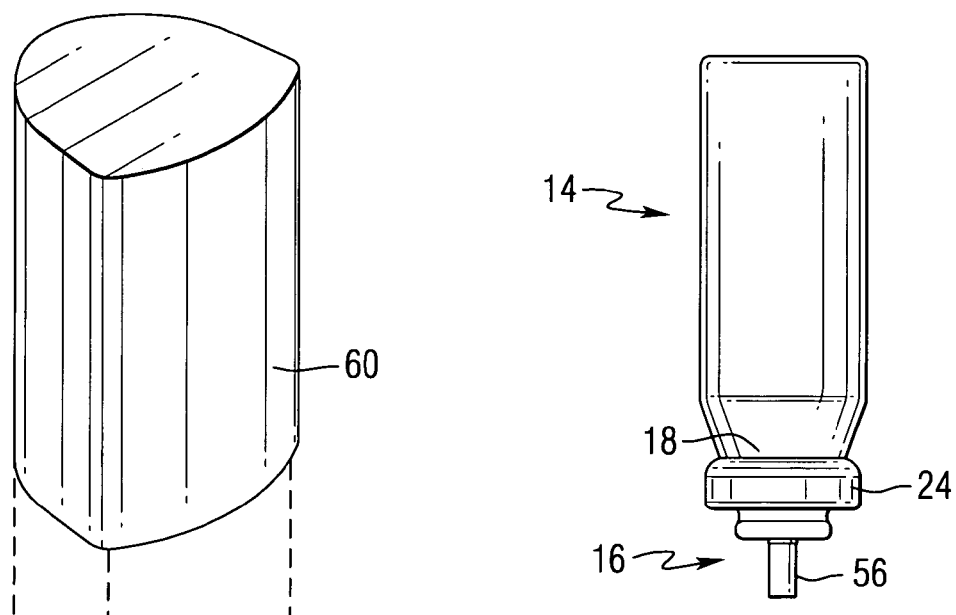
FIG. 2 is a side view of an aerosol can and metering valve assembly for a metered dose spray device of the present invention.
Figure 3:
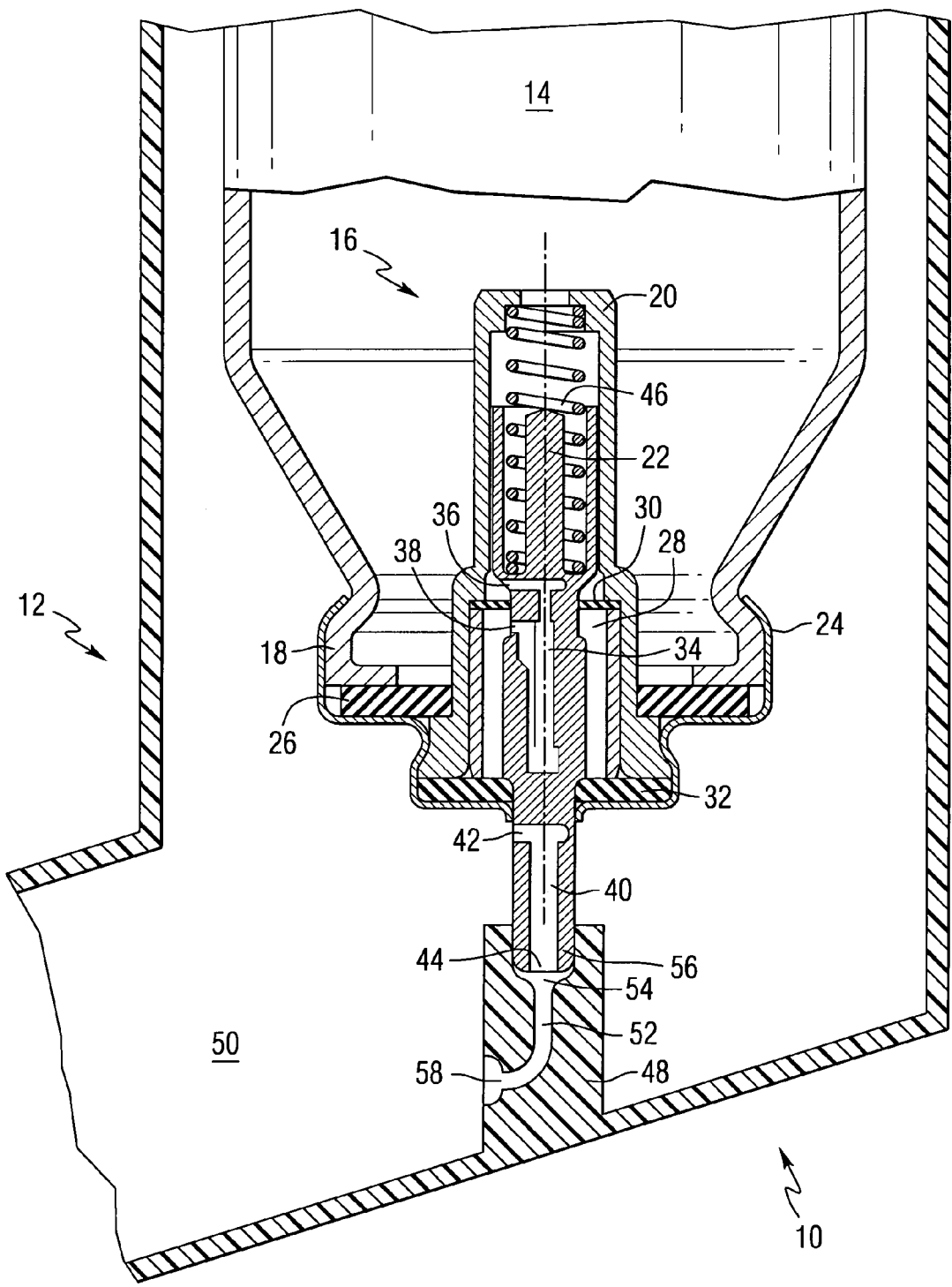
FIG. 3 is a cross-sectional side view of an actuator, aerosol can and metering valve for a metered dose spray device of the present invention, showing the metering valve at rest.
Figure 4:
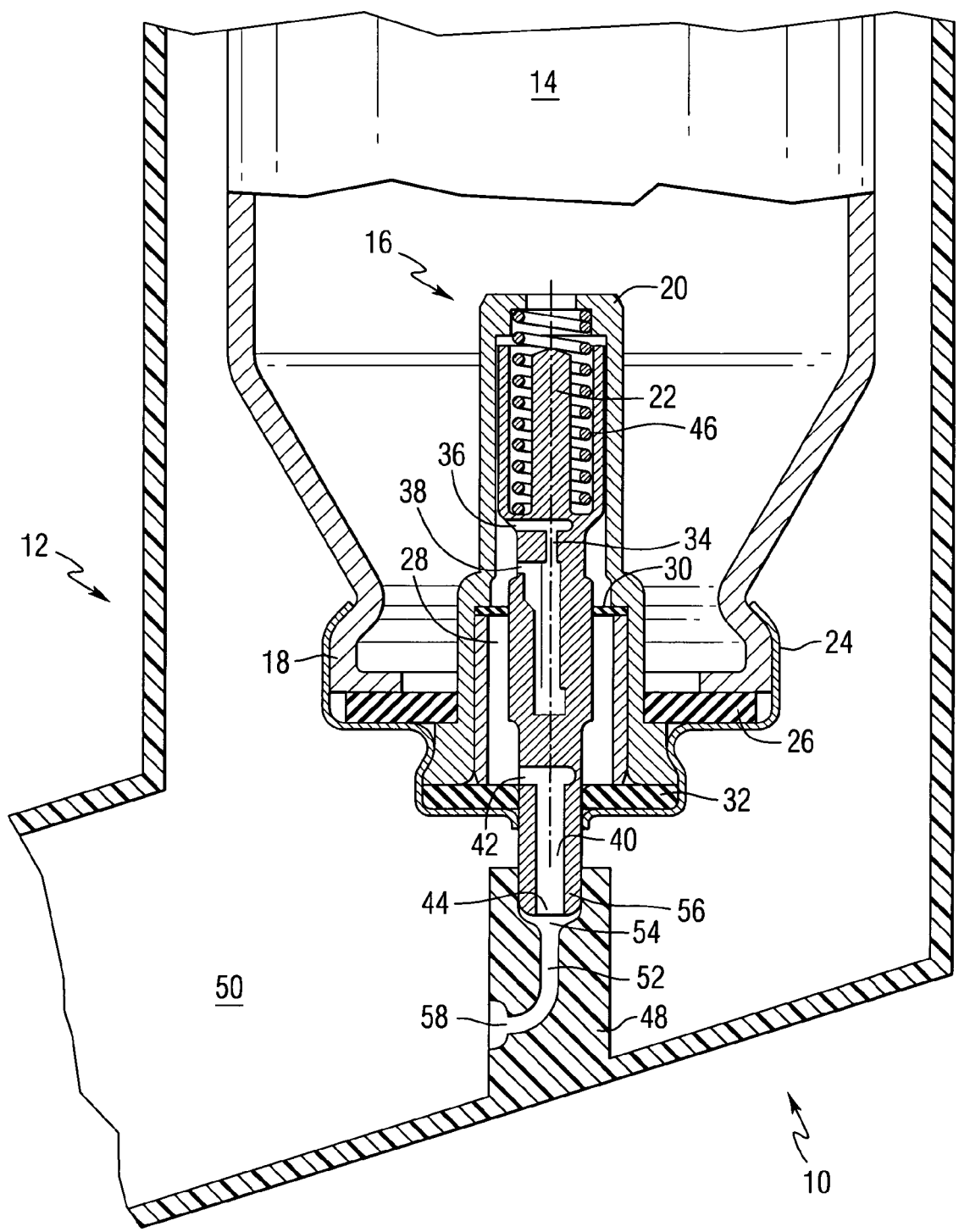
FIG. 4 is a side cross-sectional view of an actuator, can and metering valve for a metered dose spray device of the present invention, showing the metering valve open.

The aerosol can 14 is best illustrated in FIGS. 2–4. The aerosol can 14 is preferably cylindrical having an open end 18. The open end 18 is dimensioned and configured to mate with the ferrule (described below) of the metering valve 16. A preferred material for the can 14 is aluminum, but stainless steel can also be used.

Referring to FIGS. 3–4, the metering valve 16 includes a 3-slot housing 20 with a stem 22 slidably contained therein. A preferred material for the 3-slot housing and stem is Polyester, but acetal resins can be used as well. The metering valve 16 also includes a ferrule 24, dimensioned and configured to fit around the outside of the open end 18 of the aerosol can 14, being crimped around the end 18 to secure the metering valve to the can. A preferred material for the ferrule is Aluminum. A sealing gasket 26 provides a seal between the can's open end 18 and the ferrule 24. A preferred material for the sealing gasket is Nitrile (Buna) rubber. A metering chamber 28 within the 3-slot housing 20 is defined between the first stem gasket 30 and the second stem gasket 32. A preferred material for the first and second stem gaskets is Nitrile (Buna) rubber. The stem includes an upper stem and a lower stem, with the lower stem having a U-shaped retention channel 34 having ends 36 and 38, and the an upper stem having a channel 40 having ends 42 and 44. The principle of retention lies in the particular geometry at the base of the stem, which allows the passage of the fluid under the differential pressure from the aerosol can to valve metering chamber after actuation, but prevents the return (due to gravity) of the fluid to the aerosol can by the capillary action of the retention channel.

The stem 22 moves between the rest (closed) position and an open position. Within the rest position, shown in FIG. 3, the inlet end 36 of the retention channel 34 is above the first stem gasket 30, so that the contents of the aerosol can 14 may enter the retention channel 34. The outlet end 38 of the retention channel 34 is below the first stem gasket 30 and within the metering chamber 28. Both the inlet end 42 and outlet end 44 of the channel 40 are outside the metering chamber 28, thereby preventing passage of fluid from the metering chamber 28 to the channel 40. In the open position, shown in FIG. 4, both the inlet end 36 and outlet end 38 of the retention channel 34 are above the first stem gasket 30 of the metering chamber 28, thereby preventing any fluid flow from the aerosol can 14 to the metering chamber 28. At the same time, the inlet end 42 of the channel 40 is above the second stem gasket 32 and inside the metering chamber 28, thereby permitting passage of fluid from the metering chamber 28 through the passage 40. The stem 22 is biased by the spring 46 into the rest position of FIG. 3. The metering chamber 28 within the metering valve 16 may hold a total volume of approximately 100 to 600 µL. Many preferred embodiments of the metering chamber 28 will hold approximately 250–300 µL, or approximately 2 to 3 times larger than the largest metering chambers currently used in metered dose devices for the delivery of pharmaceutical aerosols. The large dose is necessary because large molecules like insulin are poorly absorbed through the epithelial membrane, easily destroyed by enzymes found in saliva, and are relatively insoluble. Therefore, more medication needs to be delivered to the buccal cavity to compensate for these losses.

Figure 1:
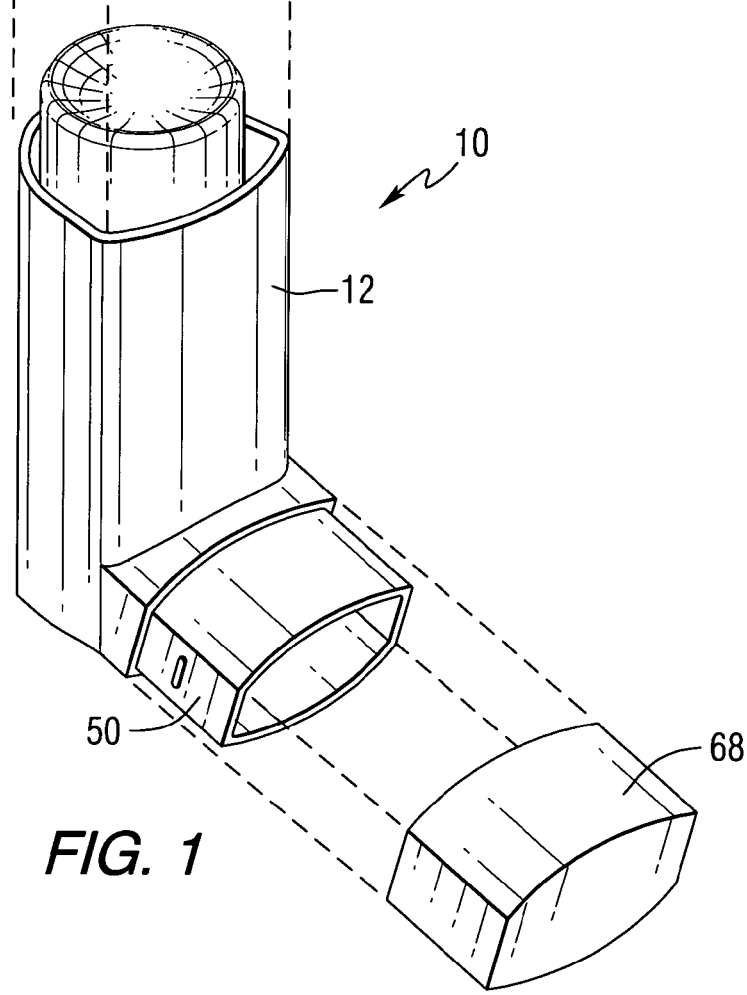
FIG. 1 is a front isometric view of a metered dose spray device according to the present invention.

The actuator assembly 12 is best illustrated in FIGS. 1, 3, and 4. The actuator 12 includes a mouthpiece 50, a stem block 48 and an actuator sump 52. The actuator sump 52, which is located in the stem block 48, includes an inlet end 54, dimensioned and configured to receive the lower end 56 of the valve stem 22, and an outlet end 58, called a spray orifice. The spray orifice 58 of the actuator sump 52 is dimensioned and configured to direct medication towards the buccal cavity and back of the throat. The spray orifice 58 may have a round configuration, or may have an oval, rectangular, or similar elongated configuration, thereby directing medication to either side of the mouth, increasing the likelihood of medication hitting the buccal cavity. Some preferred embodiments will have a spray orifice 58 having a diameter of approximately 0.58 to 0.62 mm. A preferred configuration for the actuator sump 52 is a substantially reduced volume not more than 45 mm$^3$. More preferred actuator sumps have a volume not exceeding 42 mm$^3$, and ideally the actuator sumps will have a volume not exceeding 37 mm$^3$. The sump volumes given above will be sufficient to generate a high-pressure stream of fluid upon actuation of the metered dose spray device.

The actuator 12 may also include a cap 60, fitting over the actuator 12 and aerosol can 14. The cap 60 is preferably slidably and removably secured to the actuator 12. One method of slidably and removably securing the cap 60 to the actuator 12 is by friction, thereby permitting removal or reattachment of the cap 60 and actuator 12 by merely pulling upward on the cap 60. The actuator 12 may also include a dust cover 68, dimensioned and configured to cover the mouthpiece 50.

A metered dose spray device 10 is particularly useful for administering macromolecular pharmaceutical agents such as insulin to the buccal cavity of a patient's mouth. The buccal cavity and also the back of the throat have trillions of blood vessels which may absorb insulin applied to this location, thereby eliminating the necessity of administering insulin by injection. Accordingly, the present invention is further directed to a metered dose spray device comprising an insulin propellant and a means for dispensing the insulin to the buccal cavity of a user's mouth.

Preferably, the insulin solution comprises an effective amount of insulin (or other pharmaceutical agent); an alkali metal alkyl sulfate; at least three additional absorption enhancing compounds selected from the group consisting of lecithin, hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogues thereof and mixtures or combinations thereof; and a suitable solvent. The alkali metal alkyl sulfate concentration is between about 0.1 and 20 wt./wt. % of the total composition, each absorption enhancing compound concentration is between about 0.1 and 20 wt./wt. % of the total composition, and the total concentration of the alkali metal alkyl sulfate and the absorption enhancing compounds together is less than 50 wt./wt. % of the composition.

As used herein, the term "macromolecular" refers to pharmaceutical agents having a molecular weight greater than about 1000 daltons; preferably the macromolecular pharmaceutical agents of the present invention have a molecular weight between about 2000 and 2,000,000 daltons, although even larger molecules are also contemplated.

The term "pharmaceutical agent" as used herein covers a wide spectrum of agents, and can include agents used for treatment and study for both human and veterinary applications. The term broadly includes proteins, peptides, hormones, vaccines and drugs.

Preferred pharmaceutical agents include insulin, heparin, low molecular weight heparin (molecular weight less than about 5000 daltons), hirulog, hirugen, huridine, interferons, cytokines, mono and polyclonal antibodies, immunoglobins, chemotherapeutic agents, vaccines, glycoproteins, bacterial toxoids, hormones, calcitonins, glucagon like peptides (GLP-1), large molecular antibiotics (i.e., greater than about 1000 daltons), protein based thrombolytic compounds, platelet inhibitors, DNA, RNA, gene therapeutics, antisense oligonucleotides, opioids, narcotics, hypnotics, steroids and pain killers.

Hormones which may be included in the present compositions include but are not limited to thyroids, androgens, estrogens, prostaglandins, somatotropins, gonadotropins, erythropoetin, interferons, steroids and cytokines. Cytokines are small proteins with the properties of locally acting hormones and include, but are not limited to, various forms of interleukin (IL) and growth factors including various forms of transforming growth factor (TGF), fibroblast growth factor (FGF) and insulin-like growth factor (IGF). Vaccines which may be used in the compositions according to the present invention include bacterial and viral vaccines such as vaccines for hepatitis, influenza, tuberculosis, canary pox, chicken pox, measles, mumps, rubella, pneumonia, BCG, HIV and AIDS; bacterial toxoids include but are not limited to diphtheria, tetanus, *Pseudomonas* sp. and *Mycobacterium tuberculosis*. Examples of drugs, more specifically cardiovascular or thrombolytic agents, include heparin, hirugen, hirulos and hirudine. Macromolecular pharmaceutical agents included in the present invention further include monoclonal antibodies, polyclonal antibodies and immunoglobins. This list is not intended to be exhaustive.

A preferred macromolecular pharmaceutical agent according to the present invention is insulin, upon which this description is primarily based. "Insulin" as used herein encompasses naturally extracted human insulin, or competently produced human insulin, insulin extracted from bovine, porcine or other mammalian sources, recombinantly produced human, bovine, porcine or other mammalian insulin, insulin analogues, insulin derivatives, and mixtures of any of these insulin products. The term further encompasses the insulin polypeptide in either its substantially purified form, or in its commercially available form in which additional excipients are added. Various forms of insulin are widely commercially available. An "insulin analogue" encompasses any of the insulins defined above wherein one or more of the amino acids within the polypeptide chain has been replaced with an alternative amino acid, wherein one or more of the amino acids have been deleted, or wherein one or more amino acids is added. "Derivatives" of insulin refers to insulin or analogues thereof wherein at least one organic substituent is bound to one or more of the amino acids in the insulin chain.

The insulin in the present solution becomes "encapsulated" in the various absorption enhancing compounds. As used herein, "encapsulated" is not used in its literal sense, but rather is used to refer to an array or structure formed between the insulin and one or more of the absorption enhancing compounds. For example, the "array" can be a micelle, an aggregate of micelles, or uni- or multilamellar vesicles.

It is believed that the presence of the arrays in the present compositions significantly aids in the absorption of the insulin by virtue of both their enhanced absorption ability and their size. The particle size of the micelles and vesicles will typically be in the range of 1 to 10 nanometers; many will range between 1 and 5 nanometers in size. Aggregates of micelles will be comprised of micelles each of which is about 1–10 nm in size. The shape of the array can vary and can be, for example, prolate, oblate or spherical; spherical arrays are most typical. In addition, encapsulating pharmaceutical agents in the present absorption enhancing compounds protects the agents from rapid degradation in the GI environment. It is believed that the metered dose spray device improves the absorption of the pharmaceutical agents by optimizing the spray for maximum impact in the buccal cavity. The metered dose spray device creates droplets that are of an ideal size for absorption into the buccal mucosa but too large for inhalation to the lungs, as well as a spray pattern that increases the deposition of the medication in the buccal cavity. The metered dose spray is designed for precise dosage delivery of formulation, much higher than that found in conventional metered dose inhalers.

An effective amount of insulin should be included in the present composition, such that the desired amount of insulin is delivered upon each actuation of the device. As used herein, the term "effective amount" refers to that amount of the pharmaceutical agent needed to bring about the desired result. Therefore, an effective amount of insulin is that amount of insulin needed to bring about the desired level of insulin in the patient. Such an amount will therefore be understood as having a therapeutic and/or prophylactic effect in a patient. As used herein, the term "patient" refers to members of the animal kingdom, including but not limited to humans. It will be appreciated that the effective amount, the nature and severity of the disorder being treated and the patient being treated. The determination of what constitutes an effective amount is well within the skill of one practicing in the art. Typically, the present formulations will contain insulin in a concentration between about 0.1 and 20 wt./wt. % of the total composition, more preferably between about 1 and 10 wt./wt. %.

Any alkali metal alkyl sulfate can be used in the present compositions, provided compatibility problems do not arise. Preferably, the alkyl is a C8 to C22 alkyl, more preferably lauryl (C12). Any alkali metal can be utilized, with sodium being preferred. The alkali metal alkyl sulfate is generally present in a concentration of between about 0.1 and 20 wt./wt. % of the total composition; a concentration of less than about 5 wt./wt. % of the total composition is preferred.

The compositions of the present invention further comprise at least three absorption enhancing compounds selected from the group comprising lecithin, hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate and deoxycholate. Pharmaceutically acceptable salts and analogues of any of these compounds are also within the present scope as are mixtures or combinations of any of these compounds. Each of the three, or more, absorption enhancing compounds listed above is present in the compositions in a concentration of between about 0.1 and 20 wt./wt. % of the total composition. More preferably, each of these absorption-enhancing compounds is present in a concentration of less than about 5 wt./wt. % of the total composition. For delivery of insulin, use of three or more absorption enhancing compounds achieves a synergistic effect in which the amount of pharmaceutical agent that can be delivered is greatly increased as compared to when only one or two absorption enhancing compounds are used. Use of three or more absorption enhancing compounds also enhances the stability of the pharmaceutical agent compositions.

The alkali metal alkyl sulfate functions as an absorption enhancing agent, and is added to the composition in addition to the three or more other absorption enhancing compounds listed herein. The total concentration of alkali metal alkyl sulfate and the three or more additional absorption enhancing compounds together is less than 50 wt./wt. % of the composition.

It will be appreciated that several of the micelle forming compounds are generally described as fatty acids, bile acids, or salts thereof. The best micelle-forming compounds to use may vary depending on the pharmaceutical agent used and can be readily determined by one skilled in the art. In general, bile salts are especially suitable for use with hydrophilic drugs and fatty acid salts are especially suitable for use with lipophilic drugs. Because the present invention uses relatively low concentrations of bile salts, problems of toxicity associated with the use of these salts is minimized, if not avoided.

The lecithin can be saturated or unsaturated, and is preferably selected from the group consisting of phosphatidyleholine, phosphatidylserine, sphingomyelin, phosphatidylethanolamine, cephalin, and lysolecithin.

Preferred salts of hyaluronic acid are alkali metal hyaluronates, especially sodium hyaluronate, alkaline earth hyaluronates, and aluminum hyaluronate. When using hyaluronic acid or pharmaceutically acceptable salts thereof in the present composition, a concentration of between about 0.1 and 5 wt./wt. % of the total composition is preferred, more preferably less than about 3.5 wt. /wt. %.

Particularly suitable absorption enhancing compound combinations include i) sodium hyaluronate, monoolein and saturated phospholipid, ii) saturated phospholipid, monoolein and glycolic acid, iii) sodium hyaluronate, polyoxyethylene ether and lecithin, iv) polyoxyethylene ether, trihydroxy oxocholanyl glycine and lecithin, v) polidocanol 9 lauryl ether, polylysine and triolein, vi) saturated phospholipid, polyoxyethylene ether and glycolic acid, vii) trihydroxy oxocholanyl glycine, lecithin and chenodeoxycholate; viii) trihydroxy oxocholanyl glycine, deoxycholate and glycerin; ix) polidocanol 10 lauryl ether, sodium oxocholanyl glycine and lecithin; x) polidocanol 10 lauryl ether, phosphatidyl choline and oleic acid; xi) polidocanol 10 lauryl ether, sodium hyaluronate and lecithin; and xii) polidocanol 20 lauryl ether, evening of primrose oil and lecithin.

The above-described components of the present composition are contained in a suitable solvent. The term "suitable solvent" is used herein to refer to any solvent in which the components of the present invention can be solubilized, in which compatibility problems do not arise, and which can be administered to a patient. Any suitable aqueous or nonaqueous solvent can be used. A particular preferred solvent is water. Other suitable solvents include alcohol solutions, especially ethanol. Alcohol should be used at concentrations that will avoid precipitation of the components of the present compositions. Enough of the solvent should be added so that the total of all of the components in the composition is 100 wt./wt. %, i.e., solvent to q.s. Typically, some portion of the solvent will be used initially to solubilize the pharmaceutical agent prior to the addition of the absorption enhancing compounds.

The present compositions optionally contain a stabilizer and/or a preservative. Phenolic compounds are particularly suited for this purpose as they not only stabilize the composition, but they also protect against bacterial growth and help absorption of the composition. A phenolic compound will be understood as referring to a compound having one or more hydroxy groups attached directly to a benzene ring. Preferred phenolic compounds according to the present invention include phenol and methyl phenol (also known as m-cresol), and mixtures thereof.

The compositions of the present invention can further comprise one or more of the following: inorganic salts; antioxidants; protease inhibitors; and isotonic agents. The amount of any of these optional ingredients to use in the present compositions can be determined by one skilled in the art. It will be understood by those skilled in the art that colorants, flavoring agents and non-therapeutic amounts of other compounds may also be included in the formulation. Typical flavoring agents are menthol, sorbitol and fruit flavors. When menthol is used as one of the absorption enhancing compounds, therefore, it will also impart flavor to the composition.

For example, some compositions, including those which contain insulin, may also contain at least one inorganic salt; the salt should be one which opens channels in the GI tract and which may provide additional stimulation to release insulin. Non-limiting examples of inorganic salts are sodium, potassium, calcium and zinc salts, especially sodium chloride, potassium chloride, calcium chloride, zinc chloride and sodium bicarbonate.

It will be recognized by those skilled in the art that for many pharmaceutical compositions it is usual to add at least one antioxidant to prevent degradation and oxidation of the pharmaceutically active ingredients. The antioxidant can be selected from the group consisting of tocopherol, deteroxime mesylate, methyl paraben, ethyl paraben, ascorbic acid and mixtures thereof, as well as other antioxidants known in the pharmaceutical arts. A preferred antioxidant is tocopherol. The parabens will also provide preservation to the composition.

Protease inhibitors serve to inhibit degradation of the pharmaceutical agent by the action of proteolytic enzymes. When used, protease inhibitors are preferably in a concentration of between about 0.1 and 3 wt./wt. % of the composition. Any material that can inhibit proteolytic activity can be used, absent compatibility problems. Examples include but are not limited to bacitracin and bacitracin derivatives such as bacitracin methylene disalicylates, soybean trypsin, and aprotinin. Bacitracin and its derivatives are preferably used in a concentration of between 1.5 and 2 wt./wt. % of the total composition, while soyabean trypsin and aprotinin are preferably used in a concentration of between about 1 and 2 wt./wt. % of the total composition.

An isotonic agent such as glycerin or dibasic sodium phosphate may also be added after formation of the mixed array composition. The isotonic agent serves to keep the arrays in solution. When glycerin is used as one of the absorption enhancing compounds it will also function as an isotonic agent. When dibasic sodium phosphate is used it will also serve to inhibit bacterial growth.

The pH of the present pharmaceutical composition should typically be in the range of 5 to 8, more preferably 6 to 7. Hydrochloric acid or sodium hydroxide can be utilized to adjust the pH of the composition as needed.

Propellants commonly used in conjunction with drug delivery via metered dose spray devices are also appropriate for use with the present metered dose delivery devices. It is believed that improved penetration and absorption of the pharmaceutical compositions, especially the insulin formulation described above, can be achieved by administering the present compositions with propellants such as tetrafluoroethane, heptafluoroethane, dimethylfluoropropane, tetrafluoropropane, butane, isobutane, dimethyl ether and other non-CFC and CFC propellants. Preferably, the ratio of pharmaceutical agent to propellant is from 5:95 to 25:75. The preferred propellants are hydrogen-containing chlorofluorocarbons, hydrogen-containing fluorocarbons, dimethyl ether and diethyl ether. Even more preferred is HFA-134a (1,1,1,2-tetrafluoroethane).

Use of the metered dose spray device 10 begins with the valve 16 in its rest position. When the valve 16 is in its rest position as shown in FIG. 3, medication within the aerosol can 14 is free to move through openings within the metering valve's 3-slot housing 20 (not shown, but well known in the art), through the U-shaped retention channel 34, and into the metering chamber 28. The propellant, specifically selected for its high vapor pressure, evaporates to the maximum extent permitted by the volume of the aerosol can 14. The medication within the aerosol can 14 is thereby forced through the retention channel 34 until the metering chamber 28 is full. The elongated and curved shape of the retention channel 34 keeps the medication in the metering chamber 28 from traveling back into the aerosol can 14. The location of the channel 40 below the second stem gasket 32 prevents medication from exiting the metering chamber 28 prematurely.

To use the metered dose spray device 10, the lower end 56 of the stem 22 is first inserted into the inlet end 54 of the actuator sump 52, located in the stem block 48 of the actuator. The cap 60 may be placed on top of the actuator 12, thereby completely concealing the aerosol can 14. The dust cover 68 is removed from the mouthpiece 50. The mouthpiece 50 is inserted into the user's mouth and the aerosol can 14 is depressed towards the actuator 12. This action causes the metering valve 16 to move from its rest position of FIG. 3 to its open position of FIG. 4. When the stem 22 is moved from the rest position of FIG. 3 to the open position shown in FIG. 4, the outlet opening 38 of the retention channel 34 is moved above the first stem gasket 30, thereby preventing medicine from moving from the aerosol can 14 to the metering chamber 28. At the same time, the inlet end 42 of the channel 40 is brought above the second stem gasket 32, thereby providing a path from the metering chamber 28, through the channel 40 and actuator sump 52, spray orifice 58, through the mouthpiece 50, and into the user's mouth. Opening the metering valve 16 also decreases the pressure within the metering chamber 28, causing the propellant in the metering chamber 28 to evaporate, thereby pushing the medication out through the channel 40 into the actuator sump 52, where it undergoes further evaporation as it attempts to fill the chamber and displace the air, and finally through spray orifice 58 and out the mouthpiece 50. The relatively large amount of insulin solution and propellant that may be contained within the metering chamber 28, combined with the relatively small volume of the actuator sump 52, causes the insulin solution to exit the metered dose spray device at high velocity and pressure, thereby causing the insulin solution to reach the buccal cavity and back of the throat where it may be absorbed by the patient. The droplets dispensed may be approximately 8–10 microns in size, reducing the chances of inhalation into the lungs. Releasing downward pressure on the aerosol can 14 causes the metering valve 16 to return to its rest position under pressure from the spring 46, thereby permitting a new dosage of medication to enter the metering chamber through the retention channel 34, under pressure from the evaporated propellant within the aerosol can 14.

When desired, the cap 60 may be removed, thereby permitting the aerosol can 14 to be removed from the actuator 12. The actuator 12 may thereby be easily cleaned.

While a specific embodiment of the invention has been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

The present device offers a number of benefits to the user. For example, the present a metered dose device has the ability to deliver a precise amount of medication with each application; in addition, the potential for contamination is minimized because the devices are self-contained. Finally, the device itself aids in the absorption of the pharmaceutical agent because of the rate at which the agent can be delivered.

Thus, the present devices provide a means for delivering macromolecular pharmaceutical agents, such as insulin, thereby offering a tremendous advantage to patients requiring frequent doses of these medications.

The present invention, therefore, provides novel metered dose spray devices that provide for the delivery of a macromolecular (i.e., having a molecular weight of at least 1000 daltons) pharmaceutical agents. In one embodiment these agents are encapsulated in arrays formed by a combination of absorption enhancing agents. Insulin is a preferred pharmaceutical agent. The present devices allow for delivery of pharmaceutical agents to the oral mucosae, which refers collectively to the sublingual mucosa and buccal mucosa. Drugs administered through the oral mucosa have a rapid drug absorption and a rapid onset of action, provide therapeutic plasma levels, avoid the first pass effect of hepatic metabolism, and avoid exposure of the drug to the hostile GI environment. An additional advantage is the easy access to membrane sites, so that the drug can be applied, localized and removed easily.

What is claimed is:

1. A metered dose spray device for dispensing an effective amount of a macromolecular pharmaceutical agent against the oral mucosa of a user's mouth, comprising:
   a container for housing a solution comprising a macromolecular pharmaceutical agent and a propellant,
   a metering valve coupled to the container and having a metering chamber with a volume of from 100 μl to 600 μl;
   an actuator coupled to the metering valve and having an actuator sump with a volume of less than 45 mm$^3$, the actuator sump defining at one end thereof a discharge orifice having a diameter of about 0.58 mm to 0.62 mm in communication with the atmosphere;
   wherein said metering valve is movable between a closed position in which the metering chamber is in fluid communication with the container but not the actuator sump such that a solution comprising a macromolecular pharmaceutical agent and a propellant housed in the container can flow into the metering chamber from the container, and an open position in which. the metering chamber is in fluid communication with the actuator sump but not the container such that a solution comprising a macromolecular pharmaceutical agent and a propellant contained in the metering chamber can flow into the actuator sump and be aerosolized by expansion of the propellant therein.

2. The metered dose spray device according to claim 1, comprising a solution comprising:
   an effective amount of insulin;
   an alkali metal alkyl sulfate;
   at least three absorption enhancing compounds selected from the group consisting of lecithin, hyaluronic acid, glycolic acid, lactic acid, chamomile extract, cucumber extract, oleic acid, linolenic acid, monoolein, monooleates, monolaurates, borage oil, evening of primrose oil, menthol, trihydroxy oxo cholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogues thereof, and mixtures or combinations thereof; and
   a suitable solvent;
   wherein the alkali metal alkyl sulfate and absorption enhancing compounds are each present in a concentration of between about 0.1 and 20 wt./wt. % of the total composition, and the total concentration of the alkali metal alkyl sulfate and absorption enhancing compounds together is less than 50 wt./wt. % of the total composition.

3. The metered dose spray device according to claim 2, wherein the alkali metal alkyl sulfate is in a concentration of less than about 5 wt./wt. % of the total composition.

4. The metered dose spray device according to claim 2, wherein the alkali metal alkyl sulfate is an alkali metal C8 to C22 alkyl sulfate.

5. The metered dose spray device according to claim 4, wherein the alkali metal C8 to C22 alkyl sulfate is sodium lauryl sulfate.

6. The metered dose spray device according to claim 2, wherein each of said three or more absorption enhancing compounds is present in a concentration of between about 0.1 and 5 wt./wt. % of the total composition.

7. The metered dose spray device according to claim 2, wherein the three absorption enhancing compounds are trihydroxy oxo cholanyl gylcine, polyoxyethylene ether and lecithin.

8. The metered dose spray device according to claim 2, wherein the three absorption enhancing compounds are trihydroxy oxo cholanyl cholanyl glycine, deoxycholate and glycerin.

9. The metered dose spray device according to claim 2, wherein the three absorption enhancing compounds are polidocanol 9 lauryl ether, polylysine and triolein.

10. The metered dose spray device according to claim 2, wherein the pharmaceutical agent is encapsulated in an array between about 1 and 10 nanometers in size.

11. The metered dose spray device according to claim 2, wherein said solvent is water.

12. The metered dose spray device according to claim 1, comprising 1,1,1,2-tetrafluoroethane.

13. The metered dose spray device according to claim 1, comprising an insulin solution and a propellant.

14. The metered dose spray device according to claim 1, wherein said actuator sump has a volume not exceeding 37 mm$^3$.

15. The metered dose spray device according to claim 1, wherein said metering chamber has a volume of about 250 μl to 300 μl.

* * * * *